United States Patent

Torii et al.

[11] Patent Number: 4,470,887
[45] Date of Patent: Sep. 11, 1984

[54] PROCESS FOR PREPARING THIAZOLINOAZETIDINONE DERIVATIVES

[75] Inventors: Sigeru Torii; Hideo Tanaka, both of Okayama; Norio Saito, Tokushima, all of Japan

[73] Assignee: Otsuka Kagaku Yakuhin Kabushiki Kaisha, Japan

[21] Appl. No.: 406,569

[22] Filed: Aug. 9, 1982

[51] Int. Cl.³ .................... C25C 1/00; C07D 99/10
[52] U.S. Cl. .................................................. 204/59 R
[58] Field of Search ....................... 204/59 R, 73 R

[56] References Cited

U.S. PATENT DOCUMENTS 4,392,923  7/1983  Torii et al. ................... 204/59 R

FOREIGN PATENT DOCUMENTS 57-29587  2/1982  Japan ............................ 204/73 R Primary Examiner—John F. Niebling
Attorney, Agent, or Firm—Larson and Taylor

[57] ABSTRACT

This invention provides a process for preparing a thiazolinoazetidinone derivative represented by the formula

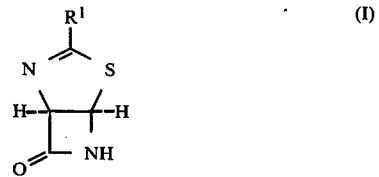

wherein $R^1$ represents a hydrogen atom, alkyl group, alkenyl group, aralkyl group, aryl group or aryloxymethyl group, the process comprising electrolyzing in a solvent a compound represented by the formula

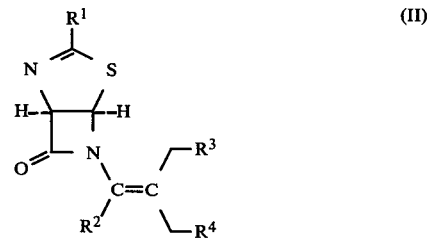

wherein $R^1$ is as defined above, $R^2$ represents a carboxyl group or protected carboxyl group, and $R^3$ and $R^4$ represent a hydrogen atom, halogen atom or acetoxy group.

9 Claims, No Drawings

PROCESS FOR PREPARING THIAZOLINOAZETIDINONE DERIVATIVES

This invention relates to a process for preparing thiazolinoazetidinone derivatives, and particularly to a process for preparing thiazolinoazetidinone derivatives represented by the formula

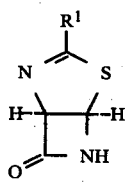
(I)

wherein $R^1$ represents a hydrogen atom, alkyl group, alkenyl group, aralkyl group, aryl group or aryloxymethyl group.

The compounds of the formula (I) are known and useful as the intermediates for synthesizing known penicillin-type or cephalosporin-type compounds. The known penicillin-type and cephalosporin-type compounds are those represented by the formula (A) and (B), respectively.

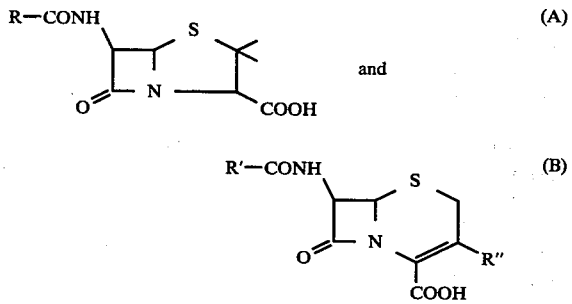

wherein R is benzyl, phenoxymethyl, α-aminobenzyl or p-hydroxy-α-aminobenzyl, R′ is p-hydroxy-α-aminobenzyl, 2-thienylmethyl, α-aminobenzyl, and R″ is 1-methyl-1H-tetrazol-5-yl-thiomethyl, hydroxyl, chloro, acetoxymethyl or methyl.

The compounds of the formulae (A) and (B) are known to have physiological activity and to be useful as antibiotics, especially as anti-bacterial agents.

The compounds of the formula (I) can be converted into the compounds of the formula (A) or (B), for example, by the process disclosed in U.S. Pat. No. 3,487,074, British Pat. No. 1,155,024, etc.

The compounds of the formula (I) are also usable for synthesizing various kinds of novel cephalosporin derivatives.

According to conventionally known processes for preparing the compounds of the formula (I), a compound of the following formula (II) is used as the staring material

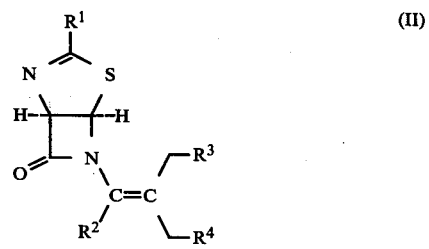

wherein $R^1$ is as defined above, $R^2$ represents a carboxyl group or protected carboxyl group, and $R^3$ and $R^4$ represent a hydrogen atom, halogen atom or acetoxy group. Stated more specifically, these conventional processes include: (1) a process in which the compound of the formula (II) is treated with lead tetracetate (Japanese Unexamined Patent Publication No. 17791/1972); (2) an ozonolysis process in which ozone is permitted to act on the compound of the formula (II) (Japanese Unexamined Patent Publication No. 17792/1972); (3) a process in which osmium tetroxide, potassium permanganate or like oxidizing agent is allowed to act on the compound of the formula (II) (Chem. Commun. 1972, 229); (4) a process in which diazomethane is permitted to act on the compound of the formula (II), thereby producing an addition product which, in turn, is subjected to a reductive cleavage reaction (Chem. Commun. 1971, 845), etc. These processes necessitate the use of highly toxic reagents, or entail a number of complicated procedures, or are low in selectivity, and are therefore undesirable as a method of mass-producing the compound of the formula (I).

It is an object of this invention to provide a process for preparing the compounds of the formula (I) which is free from the drawbacks of known processes and which is advantageous to the mass production of the compounds of the formula (I).

It is another object of this invention to provide a process for preparing the compounds of the formula (II) which does not necessitate the use of any reagent having high toxicity.

It is a further object of the invention to provide a process for preparing the compounds of the formula (II) by an extremely simple procedure.

It is a still further object of the invention to provide a process for preparing the compounds of the formula (II) in high selectivity.

These objects and other features of the invention will become apparent from the following description.

This invention provides a process for preparing thiazolinoazetidinone derivatives represented by the formula

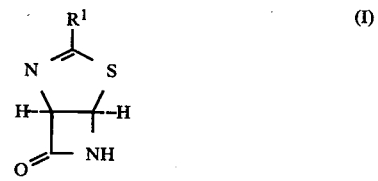
(I)

wherein $R^1$ represents a hydrogen atom, alkyl group, alkenyl group, aralkyl group, aryl group or aryloxymethyl group, the process comprising electrolyzing a compound represented by the formula

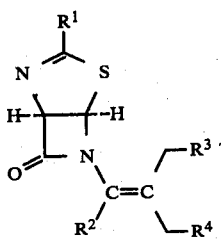

(II)

wherein R¹ is as defined above, R² represents a carboxyl group or protected carboxyl group, and R³ and R⁴ represent a hydrogen atom, halogen atom or acetoxy group in a solvent.

We have conducted extensive research on processes for converting the compounds of the formula (II) into the compounds of the formula (I). We found that when electrolyzed in a specific solvent, the starting compounds of the formula (II) can be converted directly into the compounds of the formula (I) with high selectivity by an extremely simple procedure without using any reagent of high toxicity. We also found that the electrolysis gives the compounds of the formula (I) in high yields. This invention has been accomplished based on these novel findings.

The compounds of the formula (II) serving as the starting material in the process of this invention can be prepared in high yields by a known process (as disclosed in J. Chem. Soc. (C) 1971, 3540, Tetrahedron Lett. 1970, 4897) with use of penicillin G or V or the like which can be easily produced by the fermentation method.

With respect to the meanings of R¹ of the formula (II), examples of alkyl groups are those having 1 to 12 carbon atoms, such as methyl, ethyl, propyl, hexyl, octyl, decyl, etc. Examples of the alkenyl groups are those having 2 to 12 carbon atoms, such as vinyl, allyl, propenyl, hexenyl, decenyl, etc. Examples of the aryl groups are phenyl, tolyl, xylyl, naphthyl, etc. Examples of the aralkyl groups are benzyl, p-hydroxybenzyl, etc. Examples of the aryloxymethyl groups are phenoxymethyl, tolyloxymethyl, xylyloxymethyl, naphthyloxymethyl, etc.

Exemplary of the protected carboxyl groups represented by R² in the formula (II) are salts of the formula COOM, esters of the formula COOR''', acid halides of the formula COX, acid amides of the formula CONHR¹, etc., wherein M represents a metal such as sodium, potassium, etc.; R''' represents methyl, dichloroethyl, benzyl, diphenylmethyl, p-methoxybenzyl, p-nitrobenzyl, etc.; and X is fluorine, chlorine, bromine or iodine atom.

Examples of the halogen atoms represented by R³ or R⁴ are fluorine, chlorine, bromine, iodine atoms, etc.

The compounds contemplated in this invention can be prepared by electrolyzing the compounds of the formula (II) in a solvent. Preferred examples of the solvents useful in this electrolytic reaction are carboxylic acids having 1 to 4 carbon atoms such as formic acid, acetic acid, propionic acid, etc., among which acetic acid is most preferably used. The amount of these carboxylic acid solvent to be used is about 0.1 to about 20 ml, per 0.1 m mole of the compound of the formula (II). According to this invention, a mixture of the carboxylic acid solvent and other organic solvent is usable as the solvent. Examples of the organic solvent employable as mixed with the carboxylic acid solvent are alcohols, esters of carboxylic acids, nitriles, ethers, halogenated hydrocarbons, etc. Useful alcohols include those having 1 to 5 carbon atoms such as methanol, ethanol, isopropanol, n-butanol, tert-butanol, etc. Exemplary of useful esters of carboxylic acids are alkyl esters of carboxylic acids consisting of a carboxylic acid moiety having 1 to 3 carbon atoms and an alkyl moiety having 1 to 3 carbon atoms, such as methyl acetate, ethyl acetate, methyl propionate, etc. Useful nitriles include alkyl nitriles having 2 to 5 carbon atoms such as acetonitrile, butyronitrile, etc. Useful ethers include dialkyl ethers with an alkyl moiety having 2 to 5 carbon atoms, such as diethyl ether, dibutyl ether, dipropyl ether, propyl ethyl ether, etc., or cyclic ethers such as dioxane, tetrahydrofuran, etc. Examples of useful halogenated hydrocarbons are halogenated hydrocarbons having 1 to 3 carbon atoms such as dichloromethane, dichloroethane, chloroform, carbon tetrachloride, dibromoethane, etc. Among these organic solvents, acetonitrile and ethyl acetate are preferred. When used as mixed with the carboxylic acid solvent, the organic solvent is used in an amount of up to about 500% by volume, preferably up to about 200% by volume, based on the volume of the carboxylic acid solvent.

A supporting electrolyte can be used in the electrolysis of this invention. Examples of useful supporting electrolytes are sodium acetate, potassium acetate, lithium acetate, sodium formate, sodium propionate and like alkali metal salts of carboxylic acids; triethylamine, pyridine, 2,6-lutidine, piperidine, morpholine, 1,8-diazabicyclo(5,4,0)-undecene-7(DBU) and like amines. The preferred amount of the supporting electrolyte to be used is about 0.1 to about 50 w/v %. It is favorable to employ acetic anhydride in the electrolysis. The acetic anhydride is used in an amount of about 0.1 to about 50% by volume, preferably about 1 to about 20% by volume, based on the amount of the carboxylic acid used.

Electrodes of platinum, carbon, stainless steel, lead oxide or the like which are usually used for electrolysis are usable as the anode, and those of platinum, carbon, stainless steel, nickel, copper or the like as the cathode. Preferably the platinum electrode is employed as the anode and the copper electrode as the cathode. The electrolysis is carried out at a temperature ranging from about −10° to about 60° C., preferably about 0° to about 30° C. Either an undivided electrolytic cell or an electrolytic cell divided by a diaphragm may be used in the electrolysis. Advantageously employable in this invention is an undivided electrolytic cell which need not be divided into an anode compartment and cathode compartment.

While feasible at constant voltage or controlled potential, the electrolysis can advantageously be conducted by application of a constant current at a current density of about 5 to about 500 mA/cm², preferably about 10 to about 50 mA/cm². The preferred electric charge to be passed is about 5 to about 50 F, per mole of the starting material of the formula (II), although variable depending on the type of the electrolytic cell, the kind of electrodes, the concentration of the substrate, the reactivity, etc.

After the completion of the electrolysis, the compound of the formula (I) can be isolated in high yields by conventional procedures such as solvent extraction, chromatography, etc.

The compounds of the formula (I) can be produced in high yields according to the electrolysis of this invention which is carried out by passing the required amount of current through the reaction mixture at room temperature and atmospheric pressure without using any special reagent. Thus the process of this invention is suitable for mass production of the compounds.

This invention will be described below in detail with reference to Examples.

EXAMPLE 1

A 49.8 mg quantity of methyl ester of 2-(3-benzyl-7-oxo-4-thia-2,6-diazabicyclo[3,2,0]hept-2-en-6-yl)-3-methyl-2-butenoic acid was dissolved in a mixture of 5 ml of acetic acid, 5 ml of ethyl acetate, 0.5 ml of acetic anhydride and 0.5 ml of triethylamine to obtain a uniform solution. Constant-current electrolysis was conducted for 6 hours at a temperature of 0° to 4° C. and a current density of 10 mA/cm² using a platinum electrode (3 cm²) as the anode and a copper electrode (3 cm²) as the cathode. Thereafter the solvent was distilled off at reduced pressure and the residue was extracted with 30 ml of ethyl acetate. The extract was washed with water and dried over anhydrous sodium sulfate. The solvent was removed at reduced pressure and the residue was subjected to silica gel chromatography using a mixture of benzene and ethyl acetate (5:1) as the developer, giving 3-benzylthiazolinoazetidinone. Conversion: 66%. Selectivity: 93%. M.P.: 168° C.

IR(CHCl₃): 3400, 1780 cm⁻¹

NMR(CDCl₃): 3.90(2H, s, —CH₂), 5.45(1H, d, 

J = 4Hz), 6.00(1H, m, 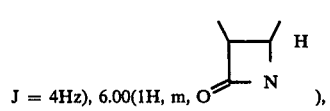), 6.70(1H, b.s, 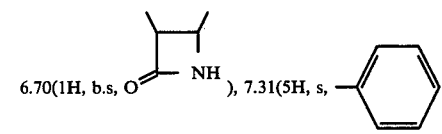), 7.31(5H, s, 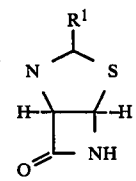)

EXAMPLES 2 TO 10

A procedure similar to that of Example 1 was performed in each of Examples 2 to 10 using a compound of the formula (1) as the starting material, whereby a compound of the formula (2) was produced. Table 1 shows the results obtained by conducting electrolysis under various conditions including concentrations of the substrates, temperatures, current densities, supporting electrodes and solvents as tabulated in Table 1.

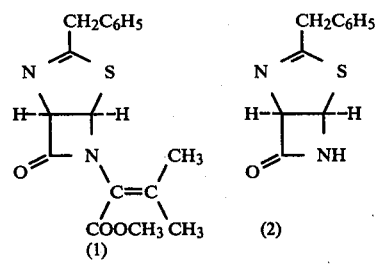

In Table 1, AcOH, AcOEt, MeOH, Et₃N and Ac₂O represent acetic acid, ethyl acetate, methanol, triethylamine and acetic anhydride, respectively.

TABLE 1

| Example | Compound (1) (mg) | Solvent (ml) | Supporting electrolyte (ml) | Additive (ml) |
|---|---|---|---|---|
| 2 | 49.2 | AcOH(5) AcOEt(5) | Et₃N(0.5) | Ac₂O(0.5) |
| 3 | 49.7 | AcOH(10) | Et₃N(0.5) | Ac₂O(0.5) |
| 4 | 49.0 | AcOH(10) | Et₃N(0.5) | Ac₂O(0.5) |
| 5 | 49.9 | AcOH(5) MeOH(5) | Et₃N(0.5) | — |
| 6 | 49.2 | AcOH(4) CH₃CN(5) | Et₃N(0.5) | Ac₂O(0.5) |
| 7 | 67.4 | AcOH(4) CH₂Cl₂(6) | Et₃N(0.5) | — |
| 8 | 56.0 | AcOH(4) AcOEt(6) | DBU(0.5) | — |
| 9 | 99.8 | AcOH(10) | 2,6-lutidine (0.45) | — |
| 10 | 51.0 | AcOH(10) | pyridine (0.5) | — |

TABLE 2

| Example | Electrode Anode | Electrode Cathode | Current density (mA/cm²) | Voltage (V) | Temp. (°C.) | Time (Hr) | Conversion (%) | Selectivity (%) |
|---|---|---|---|---|---|---|---|---|
| 2 | Pt | Cu | 20 | 34 | 0–5 | 3 | 54 | 93 |
| 3 | Pt | Cu | 20 | 9 | 18–23 | 3 | 53 | 98 |
| 4 | Pt | Cu | 20 | 6.2–6.8 | 39–43 | 3 | 68 | 73 |
| 5 | Pt | Pt | 20 | 4.5–5 | 22 | 3.4 | 56 | 76 |
| 6 | Pt | Cu | 10 | 4 | 23 | 6 | 78 | 82 |
| 7 | Pt | Pt | 40 | 22–24 | 18–20 | 3 | 63 | 87 |
| 8 | Pt | Pt | 20 | 15–17 | 16–23 | 6.6 | 90 | 76 |
| 9 | Pt | Pt | 20 | 11–9 | 16–27 | 8.7 | 77 | 73 |
| 10 | Pt | Pt | 40 | 12 | 18–23 | 1.7 | 96 | 71 |

We claim:

1. A process for preparing a thiazolinoazetidinone derivative represented by the formula wherein R¹ represents a hydrogen atom, alkyl group, alkenyl group, aralkyl group, aryl group or aryloxymethyl group, the process comprising electrolyzing in a carboxylic acid having 1 to 4 carbon atoms or a mixture of the carboxylic acid and other organic solvent and in the presence of a supporting electrolyte a compound represented by the formula

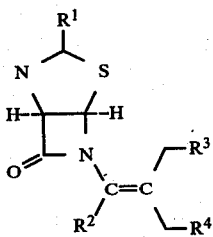

wherein $R^1$ is as defined above, $R^2$ represents a carboxyl group or protected carboxyl group, and $R^3$ and $R^4$ represent a hydrogen atom, halogen atom or acetoxy group.

2. A process as defined in claim 1 in which the solvent is a mixture of (a) carboxylic acid having 1 to 4 carbon atoms and (b) at least one member selected from the group consisting of an alcohol, ester of carboxylic acid, nitrile, ether and halogenated hydrocarbon.

3. A process as defined in claim 1 in which the solvent is used in an amount of about 0.1 to about 20 ml, per 0.1 m mole of the compound of the formula (II).

4. A process as defined in claim 1 in which the supporting electrolyte is an alkali metal salt of carboxylic acid or an amine.

5. A process as defined in claim 1 in which the supporting electrolyte is present in an amount of about 0.1 to about 50% (w/v).

6. A process as defined in claim 1 in which acetic anhydride is present in the reaction system.

7. A process as defined in claim 6 wherein acetic anhydride is present in an amount of about 0.1 to about 50% by volume, based on the amount of the carboxylic acid.

8. A process as defined in claim 1 in which the electrolysis is carried out at a current density of about 5 to about 500 mA/cm$^2$.

9. A process as defined in claim 1 in which the electrolysis is conducted at a temperature of about $-10°$ to about 60° C.

* * * * *